(12) United States Patent
Larsen

(10) Patent No.: US 9,101,723 B2
(45) Date of Patent: Aug. 11, 2015

(54) ELECTRONIC MODULE FOR MECHANICAL MEDICATION DELIVERY DEVICES

(75) Inventor: André Larsen, Dragør (DK)

(73) Assignee: Novo Nordisk A/S, Bagsvaerd (DK)

( * ) Notice: Subject to any disclaimer, the term of this patent is extended or adjusted under 35 U.S.C. 154(b) by 1410 days.

(21) Appl. No.: 12/293,252

(22) PCT Filed: Mar. 20, 2007

(86) PCT No.: PCT/EP2007/052636
§ 371 (c)(1),
(2), (4) Date: Oct. 13, 2008

(87) PCT Pub. No.: WO2007/107564
PCT Pub. Date: Sep. 27, 2007

(65) Prior Publication Data
US 2009/0069742 A1    Mar. 12, 2009

Related U.S. Application Data

(60) Provisional application No. 60/789,383, filed on Apr. 5, 2006.

(30) Foreign Application Priority Data

Mar. 20, 2006   (EP) .................................... 06005596

(51) Int. Cl.
*A61M 31/00*   (2006.01)
*A61M 5/315*   (2006.01)
(Continued)

(52) U.S. Cl.
CPC ........... *A61M 5/31593* (2013.01); *A61M 5/315* (2013.01); *G06F 19/3468* (2013.01);
(Continued)

(58) Field of Classification Search
CPC ............ A61M 2205/581; A61M 5/24; A61M 2205/50; A61M 2205/18; A61M 2205/582; A61M 2205/6018; A61M 2005/3125; A61M 2005/3126; A61M 2205/583; A61M 5/31593; A61M 2015/008; A61M 2205/3375; A61M 5/3155; A61M 5/31573; A61M 2015/007; A61M 2015/0071
USPC ......... 604/186, 207, 208, 209, 210, 211, 251, 604/407, 325, 298, 246
See application file for complete search history.

(56) References Cited

U.S. PATENT DOCUMENTS 2,807,012 A * 9/1957 Schwarz ....................... 340/609
3,844,318 A * 10/1974 Raia et al. ....................... 141/27

(Continued)

FOREIGN PATENT DOCUMENTS

DE    29904864    8/2000
DE    10116361    10/2002

(Continued)

OTHER PUBLICATIONS

International Search Report from PCT/EP2007/052636, mailed Jul. 30, 2007.

(Continued)

*Primary Examiner* — Nicholas Lucchesi
*Assistant Examiner* — William Carpenter
(74) *Attorney, Agent, or Firm* — Wesley Nicolas

(57) ABSTRACT

The present invention relates to a method for monitoring the operation of a medication delivery device. In particular, the present invention relates to a method comprising the steps of arranging an electronic module in the vicinity of the medication delivery device, detecting, using the electronic module, measurable signals generated in response to an action occurring within the associated medication delivery device, and storing, using storage means of the electronic module, information associated with or representing the measured signals. The present invention further relates to an electronic module capable of performing the above-mentioned method.

10 Claims, 2 Drawing Sheets

(51) Int. Cl.
*G06F 19/00* (2011.01)
*A61M 5/31* (2006.01)
*A61M 5/24* (2006.01)

(52) U.S. Cl.
CPC ......... *A61M 5/24* (2013.01); *A61M 2005/3126* (2013.01); *A61M 2205/3569* (2013.01); *A61M 2205/3576* (2013.01); *A61M 2205/3584* (2013.01); *A61M 2205/581* (2013.01); *A61M 2205/582* (2013.01)

(56) References Cited

U.S. PATENT DOCUMENTS

| | | | |
|---|---|---|---|
| 4,321,461 A * | 3/1982 | Walter et al. | 377/21 |
| 4,367,739 A * | 1/1983 | LeVeen et al. | 604/224 |
| 4,498,904 A * | 2/1985 | Turner et al. | 604/211 |
| 4,515,584 A | 5/1985 | Abe et al. | |
| 4,592,745 A * | 6/1986 | Rex et al. | 604/211 |
| 4,634,431 A | 1/1987 | Whitney et al. | |
| 4,636,201 A | 1/1987 | Ambrose et al. | |
| 4,747,832 A * | 5/1988 | Buffet | 604/135 |
| 4,812,724 A | 3/1989 | Langer et al. | |
| 4,838,860 A | 6/1989 | Groshong et al. | |
| 4,869,722 A * | 9/1989 | Heyman | 604/253 |
| 4,883,101 A * | 11/1989 | Strong | 141/27 |
| 4,883,472 A | 11/1989 | Michel | |
| 4,898,578 A | 2/1990 | Rubalcaba | |
| 4,959,056 A | 9/1990 | Dombrowski et al. | |
| 4,973,318 A | 11/1990 | Holm et al. | |
| 4,985,015 A | 1/1991 | Obermann et al. | |
| 4,998,570 A * | 3/1991 | Strong | 141/27 |
| 5,002,536 A | 3/1991 | Thompson et al. | |
| 5,009,640 A | 4/1991 | Pyret al. | |
| 2,017,190 A | 5/1991 | Simon et al. | |
| 5,042,977 A * | 8/1991 | Bechtold et al. | 604/134 |
| 5,098,400 A | 3/1992 | Crouse et al. | |
| 5,104,380 A * | 4/1992 | Holman et al. | 604/117 |
| 5,114,406 A * | 5/1992 | Gabriel et al. | 604/136 |
| 5,125,268 A * | 6/1992 | Caron | 73/170.17 |
| 5,221,268 A | 6/1993 | Barton et al. | |
| 5,254,102 A * | 10/1993 | Ogawa | 604/253 |
| 5,272,917 A | 12/1993 | Pippert | |
| 5,279,585 A * | 1/1994 | Balkwill | 604/207 |
| 5,279,586 A | 1/1994 | Balkwill | |
| 5,363,842 A | 11/1994 | Mishelevich et al. | |
| 5,385,559 A * | 1/1995 | Mannix | 604/211 |
| 5,494,036 A | 2/1996 | Uber, III et al. | |
| 5,509,905 A | 4/1996 | Michel | |
| 5,522,799 A | 6/1996 | Furukawa | |
| 5,536,249 A | 7/1996 | Castellano et al. | |
| 5,573,506 A | 11/1996 | Vasko | |
| 5,582,598 A | 12/1996 | Chanoch | |
| 5,591,136 A * | 1/1997 | Gabriel | 604/211 |
| 5,593,390 A | 1/1997 | Castellano et al. | |
| 5,662,612 A | 9/1997 | Niehoff | |
| 5,690,618 A | 11/1997 | Smith et al. | |
| 5,704,922 A | 1/1998 | Brown | |
| 5,725,508 A | 3/1998 | Chanoch et al. | |
| 5,728,074 A | 3/1998 | Castellano et al. | |
| 5,782,814 A | 7/1998 | Brown et al. | |
| 5,795,333 A | 8/1998 | Reilly et al. | |
| 5,807,336 A | 9/1998 | Russo et al. | |
| 5,843,047 A | 12/1998 | Pyrozyk et al. | |
| 5,873,856 A | 2/1999 | Hjertman et al. | |
| 5,920,198 A | 7/1999 | Suzuki et al. | |
| 5,928,197 A | 7/1999 | Niehoff | |
| 5,947,934 A | 9/1999 | Hansen et al. | |
| 5,998,989 A | 12/1999 | Lohberg | |
| 6,019,745 A | 2/2000 | Gray | |
| 6,113,578 A * | 9/2000 | Brown | 604/207 |
| 6,235,004 B1 | 5/2001 | Steenfeldt-Jensen et al. | |
| 6,268,722 B1 | 7/2001 | Kogure et al. | |
| 6,328,033 B1 * | 12/2001 | Avrahami | 128/203.15 |
| 6,482,185 B1 * | 11/2002 | Hartmann | 604/189 |
| 6,514,230 B1 * | 2/2003 | Munk et al. | 604/207 |
| 6,547,755 B1 | 4/2003 | Lippe et al. | |
| 7,025,743 B2 * | 4/2006 | Mann et al. | 604/66 |
| 7,138,806 B2 | 11/2006 | Gafner et al. | |
| 7,144,384 B2 | 12/2006 | Gorman et al. | |
| 7,161,488 B2 * | 1/2007 | Frasch | 340/572.1 |
| 7,195,616 B2 | 3/2007 | Diller et al. | |
| 2002/0029018 A1 | 3/2002 | Jeffrey | |
| 2003/0055685 A1 | 3/2003 | Cobb et al. | |
| 2004/0074652 A1 | 4/2004 | Ginell | |
| 2004/0171983 A1 | 9/2004 | Sparks et al. | |
| 2004/0207385 A1 | 10/2004 | Gafner et al. | |
| 2004/0210199 A1 | 10/2004 | Atterbury et al. | |
| 2005/0020969 A1 | 1/2005 | Slate et al. | |
| 2005/0041531 A1 * | 2/2005 | Sekura | 368/10 |
| 2005/0182360 A1 | 8/2005 | Yeandel et al. | |
| 2006/0047538 A1 | 3/2006 | Condurso et al. | |
| 2006/0135907 A1 * | 6/2006 | Remde et al. | 604/67 |
| 2008/0140018 A1 | 6/2008 | Enggaard et al. | |
| 2008/0188813 A1 | 8/2008 | Miller et al. | |
| 2008/0312604 A1 * | 12/2008 | Boesen | 604/207 |
| 2009/0069742 A1 | 3/2009 | Larsen | |

FOREIGN PATENT DOCUMENTS

| | | |
|---|---|---|
| DE | 10201875 | 5/2003 |
| DK | PA 2001 00240 | 11/2001 |
| EP | 387854 | 9/1990 |
| EP | 0635277 | 1/1995 |
| EP | 1074273 | 2/2001 |
| EP | 1095668 | 5/2001 |
| EP | 1361908 | 11/2003 |
| EP | 1393764 | 3/2004 |
| EP | 04077898.7 | 10/2004 |
| EP | 1726322 | 11/2006 |
| EP | 1804868 | 12/2009 |
| FR | 2740345 | 4/1997 |
| JP | H10-89910 | 4/1998 |
| JP | 10504729 | 5/1998 |
| JP | 2002531154 A | 9/2002 |
| JP | 2003-310758 | 11/2003 |
| JP | 2006507856 A | 3/2006 |
| RU | 2080882 | 6/1997 |
| SU | 1760462 | 9/1992 |
| WO | WO 90/09202 | 8/1990 |
| WO | 90/10470 | 9/1990 |
| WO | WO 95/24233 | 9/1995 |
| WO | WO 97/30742 | 8/1997 |
| WO | WO 97/33638 | 9/1997 |
| WO | WO 99/15214 | 4/1999 |
| WO | WO 01/26710 | 4/2001 |
| WO | WO 02/43573 | 6/2002 |
| WO | WO 02/064196 | 8/2002 |
| WO | 02/092153 | 11/2002 |
| WO | WO 02/092153 | 11/2002 |
| WO | WO 03/005891 | 1/2003 |
| WO | WO 03/009461 | 1/2003 |
| WO | WO 03/047426 | 6/2003 |
| WO | WO 03/103753 | 12/2003 |
| WO | 2004/030717 A2 | 4/2004 |
| WO | WO 2004/030717 | 4/2004 |
| WO | WO 2004/098390 | 11/2004 |
| WO | WO 2004/110528 | 12/2004 |
| WO | WO 2005/042076 | 5/2005 |
| WO | WO 2006/045525 | 5/2006 |
| WO | 2006087712 A2 | 8/2006 |

OTHER PUBLICATIONS

Machine Translation of German Patent 10116361, published Oct. 10, 2002.
Non-Final Office Action Mailed May 13, 2011 in U.S. Appl. No. 11/665,572, filed Apr. 17, 2007 by Enggaard et al.
Tränkler, 1996, "Taschenbuch Der Messtechnik," R. Oldenbourg Verlag München Wien pp. 181, 190.
International Search Report from PCT/EP2005/011282, Filed Oct. 20, 2005.
DE 29904864 English Abstract, published Aug. 3, 2000, DE 2904864.

(56) References Cited

OTHER PUBLICATIONS

DE 10201875 English Abstract, published May 22, 2003.
FR 2740345 English Abstract, published Oct. 26, 1995.
Final Office Action mailed Aug. 9, 2010 in U.S. Appl. No. 11/665,623, filed Feb. 4, 2008 by Miller et al.
Non-Final Office Action mailed Mar. 29, 2010 in U.S. Appl. No. 11/665,623, filed Feb. 4, 2008 by Miller et al.
Final Office Action mailed Apr. 10, 2009 in U.S. Appl. No. 11/665,623, filed Feb. 4, 2008 by Miller et al.
Non-Final Office Action mailed Oct. 27, 2008 in U.S. Appl. No. 11/665,623, filed Feb. 4, 2008 by Miller et al.
Final Office Action mailed May 14, 2009 in U.S. Appl. No. 11/665,572, filed Feb. 4, 2008 by Enggaard et al.
Non-Final Office Action mailed Sep. 19, 2008 in U.S. Appl. No. 11/665,572, filed Feb. 4, 2008 by Enggaard et al.
Notice of Allowance mailed Aug. 31, 2005 in U.S. Appl. No. 10/076,025, filed Feb. 13, 2002 by Larsen et al.
Non-Final Office Action mailed Nov. 28, 2003 in U.S. Appl. No. 10/076,025, filed Feb. 13, 2002 by Larsen et al.

* cited by examiner

ELECTRONIC MODULE FOR MECHANICAL MEDICATION DELIVERY DEVICES

CROSS-REFERENCE TO RELATED APPLICATIONS

This application is a 35 U.S.C. §371 national stage application of International Patent Application PCT/EP2007/052636 (published as WO 2007/107564), filed Mar. 20, 2007, which claimed priority of European Patent Application 06005596.9, filed Mar. 20, 2006; this application further claims priority under 35 U.S.C. §119 of U.S. Provisional Application 60/789,383, filed Apr. 5, 2006.

FIELD OF THE INVENTION

The present invention relates to an electronic module adapted to be positioned on an outer surface of a pen-like medication delivery device. In particular, the present invention relates to an electronic module capable of measuring signals, such as audible, optical, vibration or electromagnetic signal, generated during operation of a pen-like medication delivery device.

BACKGROUND OF THE INVENTION

For the users of medication delivery devices it is a cumbersome process to keep track of the amount of doses being expelled from the medication delivery device. This process is being further complicated if the time of injection, date of injection etc. are also to be monitored.

U.S. Pat. No. 6,482,185 discloses an external display apparatus for pen-like injection devices. For people with an impaired vision, the setting of a dose on a pen-like injection device may be difficult. In U.S. Pat. No. 6,482,185 an external display apparatus is provided. This display apparatus may be attached to the pen. Via contacts and counter contacts information about the dose is transmitted to the display apparatus and shown on a large display. The display apparatus suggested in U.S. Pat. No. 6,482,185 may also comprise some sort of storage arrangement which allows storage or recording of a set dose of medicament together with associated data like time, date and the kind of medicament (e.g. insulin preparation).

It is a disadvantage of the display apparatus suggested in U.S. Pat. No. 6,482,185 that it requires that the pen-like injection device to which it is intended to be attached to undergoes severe modifications in that special communication arrangements, such as electrical contacts, optical ports, gear wheels etc. are required in order to transfer information from the pen-like injection device to the display apparatus.

WO 2004/110528 relates to a device for examination of a medical device. The device suggested in WO 2004/110528 comprises an acoustic receiver which is capable of detecting sounds emitted by the medical device in order to examine the medical device for errors. WO 2004/110528 further relates to a method for examining a medical device whereby sound emitted by the medical device is detected and analysed.

The device suggested in WO 2004/110528 is intended for detecting and localising errors in medical devices. Thus, the device suggested in WO 2004/110528 forms part of a test facility for testing medical devices. The device suggested in WO 2004/110528 is unsuitable for mapping the manner of use of a medical device, such as a medication delivery device capable of delivering set doses of insulin, over a given period of time. In order to obtain reliable mapping results, such given period of time may for example be several months. The reasons why the device according to WO 2004/110528 is unsuitable for mapping the manner of use of a medical device are many. For example, the device suggested in WO 2004/110528 does not facilitate time stamping of events occurring in a medical device. This lack of time stamping makes it impossible to arrange detected events in a chronological correct order.

It is an object of the present invention to provide a portable electronic module being capable of monitoring the overall operation of standard, and thereby non-modified, medication delivery devices.

It is a further object of the present invention to provide a portable electronic module adapted to be attached to a medication delivery device without influencing or affecting daily use of the medication delivery device.

According to the present invention an electronic module capable of measuring externally accessible acoustical and/or vibrational signals generated under normal operation, such as during setting and expelling of a set dose of medicament, of a pen-like medication delivery device is suggested.

It is an advantage of the present invention that data relating to corresponding values of time/date and the amount of injected medicament may easily be transferred from the electronic module to for example a computer for further processing. In this way, traditional paper-based diary's can be avoided. In addition, the present invention can be used as an electronic logbook for conventional medication delivery devices.

SUMMARY OF THE INVENTION

The above-mentioned object is complied with by providing, in a first aspect, a method for wirelessly monitoring the operation of a mechanical medication delivery device, the method comprising the steps of
  attaching an electronic module to an associated mechanical medication delivery device using mutually cooperating coupling means for releasable coupling the electronic module to the associated mechanical medication delivery device,
  detecting, using the electronic module, measurable signals generated in response to an event or action occurring within the associated medication delivery device, and associating with each event a time stamp, and
  storing, using storage means of the electronic module, information associated with the detected measurable signals, and storing the associated time stamp
wherein the measurable signals are acoustical and/or vibrational signals.

Thus, the measurable signal may be acoustical signals generated in response to setting a dose of medicament. The dose of medicament may be set by activation of a dose setting member of the associated mechanical medication delivery device. The acoustical signals may also be generated in response to expelling a dose of medicament from the associated mechanical medication delivery device.

The method may further comprise the step of transmitting information associated with or representing the measured signals to an, in relation to the electronic module, external module, unit or portable device for further processing. The transmitting to the external module, unit or portable device may be provided by wireless means, such as Bluetooth.

By mechanical medication delivery device is meant a handheld device where the user of the device delivers the required force to expel a set dose of medicament. Alternatively, the user of the mechanical medication delivery device may energize the device by accumulating energy in an appropriate member of the mechanical medication delivery device. Such member may include a resilient member, such as a linear spring or a torsion spring.

In a second aspect, the present invention relates to a portable electronic module adapted to be releasable coupled on an associated mechanical medication delivery device, the electronic module comprising means for wirelessly detecting measurable signals generated in response to an event or action occurring within the associated mechanical medication delivery device, and associating with each event or action a time stamp, mutually cooperating coupling means for releasable coupling the electronic module to the associated mechanical medication delivery device, and means for storing information associated with the detected measurable signals, and storing the associated time stamp wherein the measurable signals are acoustical and/or vibrational signals.

Again, mechanical medication delivery device is intended to mean a handheld device where the user of the device delivers the required force to expel a set dose of medicament. Alternatively, the user of the mechanical medication delivery device may energize the device by accumulating energy in an appropriate member of the mechanical medication delivery device. Such member may include a resilient member, such as a linear spring or a torsion spring.

The electronic module may further comprise means for transmitting detected, stored or recorded information to an external module or unit for further processing. The electronic module may in addition comprise signal processor means adapted to process the detected signal or signals prior to storing information associated therewith or representing said signal or signals. The detecting means may comprise a microphone capable of detecting acoustical signals generated in the associated mechanical medication delivery device. Preferably such microphone is a miniature microphone, such as the types of microphones used in the hearing aid industry.

Alternatively or in addition, the detecting means may comprise an accelerometer capable of detecting vibrational signals generated in the associated mechanical medication delivery device.

The transmitting means may comprise means for wirelessly transmitting information from the electronic module to the external module or unit. The wireless transmitting of information from the electronic module to the external module or unit may be provided using Bluetooth.

The electronic module may further comprise display means adapted to provide visual information to the user of the electronic module, and a touch pad switch adapted to switch on the electronic module upon activation. Alternatively, contact means adapted to switch on the electronic module during normal use of the medication delivery device may be provided. Such contact means are preferably hidden within the housing of the electronic module.

BRIEF DESCRIPTION OF THE DRAWINGS

The present invention will now be explained with reference to the accompanying drawings wherein.

Figure 1:
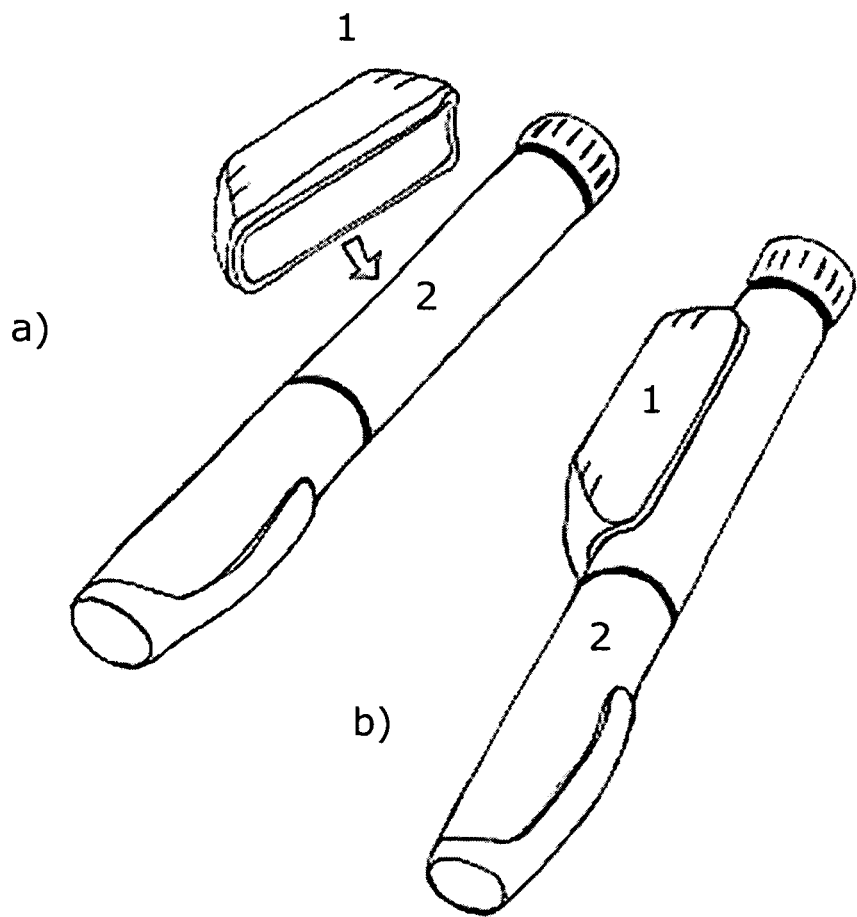
FIG. 1 shows an electronic module according to the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to a portable electronic module capable of measuring acoustical and/or vibrational signals generated in response to relative movements of internal parts constituting at least part of a mechanical medication delivery device to which the portable electronic module is attached. Such internal parts can be mechanical parts which during movements generate for example acoustical sounds, such as click sounds.

The portable electronic module according to the present invention is intended for mapping the manner of use of a medical device, such as a medication delivery device capable of delivering set doses of insulin, over a given period of time. In order to obtain reliable mapping results, such given period of time typically extends over several months. Thus, the portable electronic module according to the present invention is adapted to be attached to a medication delivery device typically for several months whereby the manner of use of the medication delivery device can be precisely mapped. In order to do this time stamping of events occurring in the medication delivery device is important in that time stamping makes it possible to arrange detected events in a chronological correct order.

The electronic module further comprises means for storing or recording information generated from the measured signals, and means for optionally transmitting such stored or recorded information to an external module or device for further processing. This external module or device can be a computer, a cellular phone, a PDA or a similar device capable of for example displaying injected doses of insulin as a function of time. Thus, by transferring the stored data to a computer the user of the medication delivery device may have his/hers injection pattern displayed on a screen, and he/she can chose to store the displayed information in the computer.

The transmitting or transferring of data from the electronic module to the computer/cellular phone/PDA can be via a wire plugged into the electronic module. Alternatively, the transmitting or transferring of data between the module and the computer/cellular phone/PDA can be accomplished by wireless means, such as DECT or Bluetooth.

In order to measure acoustical signals the electronic module comprises some sort of pressure sensor, such as a miniature microphone. The miniature microphone is capable of picking up mechanical "click sounds" generated when engaging plastic or metal parts of the medication delivery device are moved relative to each other—typically in and out of engagement.

Electronic circuits connected to the miniature microphone may assist filtering the picked-up "click sounds". Thus, if the detected "click-sound" falls within a certain frequency range, say a low frequency range, a dose of medicament is being set. Similarly, if the detected "click-sounds" falls within a high frequency range a dose of medicament is being expelled from the medication delivery device. Typically, the mechanical clicking is measured by counting the number of clicks. One click corresponds to a certain amount of for example expelled medicament. Thus, by counting the number of clicks during an expelling sequence the amount of medicament expelled from the medicament delivery device can easily be calculated.

The electronic module can also store or record a complete sequence of events. Such a sequence can for example include the switching on of the electronic module, the recording of low frequency click sounds in response to a dose being set and the recording of high frequency click sounds in response to a dose being expelled.

The electronic module also stores corresponding values of the number of click sounds and time/date. Thus, when the user of the medication delivery device transmits or transfers the stored data from the electronic module to a computer, the time, date, amount of each set dose and the amount of each injected dose may be visualized to the user of the mechanical medication delivery device.

It should be mentioned, that the electronic module according to the present invention may also measure other signals than acoustical signals. An example of such other type of signal may be vibrational signals. Obviously, if such non-acoustical signals are to be measured other types of sensors are to be applied. For example, a miniature accelerator is capable of measuring vibrational signals.

The electronic module according to the present invention may also house a signal processor for full or partial processing of measured signals. Thus, the information transmitted or transferred to external units may be raw or pre-processed data.

Referring now to FIG. 1 an electronic module 1 according to the present invention is shown. As seen in FIG. 1 the module 1 is mountable on the housing of a mechanical medication delivery device 2. The module is attached to the upper part of the medication delivery device, i.e. where the arrangement for driving a piston rod so as to expel a medicament is positioned, using magnetic means, such as permanent magnetic means, provided in the electronic module. However, other coupling arrangements between module and device are also applicable. The piston rod moves a piston of a cartridge towards a proximal end of the medication delivery device.

The module may, as already mentioned, be equipped with appropriate sensors suitable for detecting acoustical and/or vibrational signals generated in response to normal operation of the medication delivery device. For example, two meshing gear-wheels (not shown) can produce click sounds which may be recorded by a miniature pressure sensor, such as a miniature microphone, mounted in the housing of the module. The module may be adapted to process the recorded signals by for example counting the number of recorded "clicks" so that the amounts of a set dose of medicament and an expelled dose of medicament can be stored in the module. As already mentioned information stored in the module can be transferred to an external device, such as a portable computer, for further processing.

An exterior surface part of the housing of the electronic module according to the present invention may support an electrical switch and/or a display member. The electrical switch is preferably implemented as a capacitive finger touch switch. Upon activation of this switch the electronics of the electronic module is powered from a battery positioned in the housing of the electronic module. Alternatively, the electrical switch can be incorporated within the housing of the electronic module. Such an incorporated switch is activated during normal use of the mechanical medication delivery device. Thus, the user of the medication delivery device should not specifically address activation of the switch in that the switch is automatically activated when the mechanical medication delivery device is held in the hand of the user of the device. The display member can be a flat panel LCD array capable of providing valuable information to the user of the electronic module.

Figure 2:
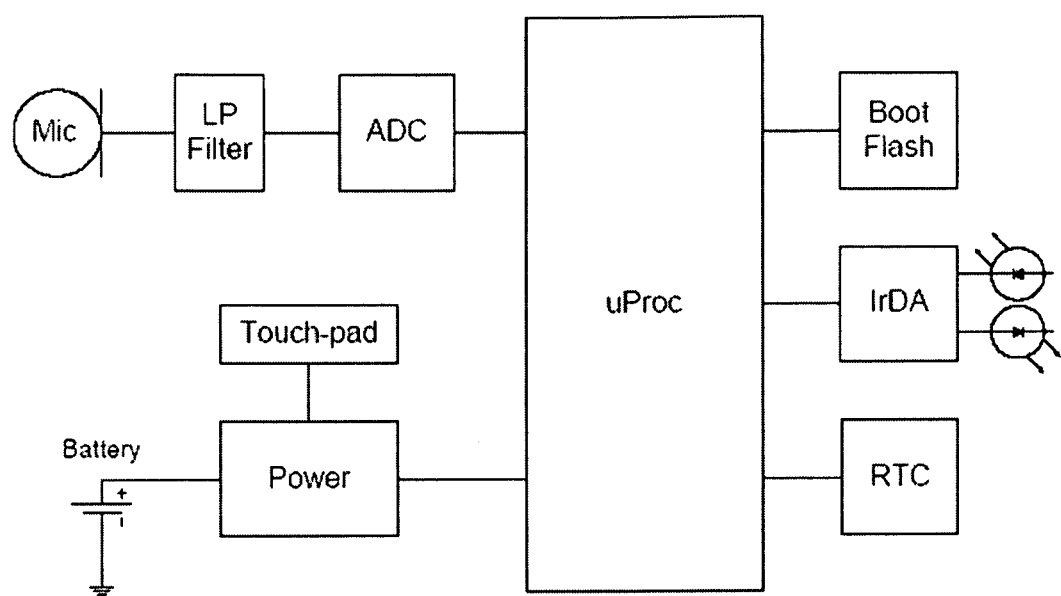
FIG. 2 shows a block diagram of a simple version of an electronic module according to the present invention.

FIG. 2 shows a block diagram of a simple version of the electronic module according to the present invention. The electronic module depicted in FIG. 2 is adapted to record acoustical click sounds generated in response to doses being set and doses being expelled. As seen, the potable electronic module comprises a microphone, a low-pass filter and an A/D converter. Thus, acoustical signals picked-up by the microphone are first low-pass filtered and then converted to a digital format before being provided to a microprocessor. In terms of power the electronic module is powered by a built-in battery which powers the module when for example a capacitive touch pad is activated. This activation is performed when for example a finger tip is positioned on the touch pad.

The microprocessor is in communication with a Boot Flash within which the control software for the microprocessor is stored. In order to communicate with the surroundings the electronic module is equipped with an optical communication port, IrDA, which allows recorded data to be communicated to an external device. Obviously, this communication with the surroundings may be accomplished by other means, such as a physical wire connecting the electronic device with the external device, Bluetooth, DECT etc. The real time clock, RTC, ensures that data relating to for example dose setting and dose expelling are stored or recorded along with time and date associated thereto. In addition, the switch-on time of the module can be stored along with these parameters.

The invention claimed is:

1. A portable handheld electronic module adapted to be releasably attached to an associated mechanical medication delivery device, said mechanical medication delivery device being configured for setting the amount of a dose of a medicament and injecting of set doses, the mechanical medication delivery device generating click sounds during setting and expelling of a dose of a medicament whereby the number of click sounds correspond to an amount of a set dose and an expelled dose, the portable electronic module comprising:
   a module housing;
   a detector mounted in the module housing for wirelessly detecting click sounds generated in response to an event or action occurring within the associated mechanical medication delivery device during the setting and/or expelling of a dose, and associating with each event or action a time stamp;
   a mutually cooperating coupling device releasably attaching the portable handheld electronic module to the associated mechanical medication delivery device; and
   a signal processor structure for storing information associated with the detected click sounds including the number of click sounds detected during setting and expelling of a dose, and storing the associated time stamp;
wherein said signal processor structure is adapted to process the detected click sounds prior to storing information associated with said click sounds, and wherein the signal processor structure is able to distinguish and process click sounds generated by way of filtering differing frequency ranges in the associated mechanical medication delivery device of wherein the signal processor structure determines whether an at least one dose of medicament is being set and an at least one dose of medicament is being expelled.

2. A portable electronic module according to claim 1, further comprising structure for transmitting stored information to an external module or unit for further processing.

3. A portable electronic module according to claim 2, wherein the detector comprises a microphone capable of detecting click sounds generated in the associated mechanical medication delivery device.

4. A portable electronic module according to claim 2, wherein the detector comprises an accelerometer capable of detecting vibrational signals generated in the associated mechanical medication delivery device.

5. A portable electronic module according to claim 2, wherein the transmitting structure comprise structure for wirelessly transmitting information from the electronic module to the external module or unit.

6. A portable electronic module according to claim 5, wherein the wireless transmitting of information from the electronic module to the external module or unit is provided by utilizing short-range radio frequency communication.

7. A portable electronic module according to claim 1, further comprising a display adapted to provide visual information to the user of the electronic module.

8. A portable electronic module according to claim 1, further comprising a touch pad switch adapted to switch on the electronic module upon activation.

9. A portable electronic module according to claim 1, further comprising a contact adapted to switch on the electronic module during normal use of the medication delivery device.

10. A portable electronic module according to claim 1, wherein the detector comprises an accelerometer capable of detecting vibrational signals generated in the associated mechanical medication delivery device.

\* \* \* \* \*